United States Patent [19]

Miller

[11] Patent Number: 5,063,063

[45] Date of Patent: Nov. 5, 1991

[54] HYPOADHERENT DRESSINGS COMPRISING LIQUID PERVIOUS POLYMER COATING OF POLYURETHANE CONTAINING SILOXANE RESIDUES

[75] Inventor: Nigel D. Miller, South Wirral, United Kingdom

[73] Assignee: Smith & Nephew plc, United Kingdom

[21] Appl. No.: 352,872

[22] Filed: May 17, 1989

[30] Foreign Application Priority Data

May 18, 1988 [GB] United Kingdom ............... 8811776

[51] Int. Cl.$^5$ ............... A61L 15/00; B32B 27/12; B32B 27/28; B32B 27/40
[52] U.S. Cl. ............... 424/445; 424/443; 604/304; 128/155; 128/156; 428/266; 428/290
[58] Field of Search ............... 424/443, 445; 428/266, 428/290

[56] References Cited

U.S. PATENT DOCUMENTS

| | | | |
|---|---|---|---|
| 2,693,438 | 11/1954 | Ward | 425/445 |
| 3,419,006 | 12/1968 | King | 425/445 |
| 4,002,171 | 1/1977 | Taft | 428/290 |
| 4,243,656 | 1/1981 | Walliczek | 424/443 |
| 4,686,137 | 8/1987 | Ward, Jr. et al. | 428/423.1 |
| 4,840,796 | 6/1989 | Sweet et al. | 424/448 |

*Primary Examiner*—Thurman K. Page
*Assistant Examiner*—E. J. Webman
*Attorney, Agent, or Firm*—Rosenman & Colin

[57] ABSTRACT

Fibrous dressings employed as wound contacting materials, may be rendered hypoadherent by coating the body contacting surface with a polymeric coating of a material such as a siloxane block copolymer or a blend thereof with an amine extended polyurethane.

12 Claims, No Drawings

HYPOADHERENT DRESSINGS COMPRISING LIQUID PERVIOUS POLYMER COATING OF POLYURETHANE CONTAINING SILOXANE RESIDUES

This invention relates to dressings and particularly to dressings containing fibrous absorbent materials for use with exuding wounds.

It is known that if an exuding wound is covered with a dressing, the dressing will adhere to the wound as the wound heals and the eschar dries. Removal of the dressing can be painful and the dressing may also be difficult to remove and cause wound damage as the re-epithelialised surface is disrupted. Significant trauma and wound damage can be expected with dressings which have a fibrous wound contacting layer.

Fibrous dressings, such as those made from gauze, have advantages which to some extent offset the disadvantages associated with their adherency to drying wounds. Generally, they are highly absorbent and thus useful for covering highly exuding wounds.

Previous attempts to arrive at a compromise between absorbency and adherency have included the impregnation of materials such as petroleum jelly into the gauze interstices, eg. as a TULLE GRAS. However, although such dressings initially have low adherence, the petroleum jelly washes out and the dressing becomes adherent.

In an alternative embodiment a film layer is provided which is intermediate to the wound and the absorbent layer. A commercially available product of the contruction comprises a multi-ply gauze bonded to a perforated layer of polyethylene terephthalate and is sold under the trade mark "Melolin" (T. J. Smith & Nephew Limited). In use the film side of the dressing is applied to the wound. A disadvantage associated with such a multilayer construction is the cost of manufacture.

We have now found that hypoadherent dressings comprising a fibrous body-facing or wound contacting substrate can be produced which dressings require less energy to separate them directly from wound eschar than that required for conventional dressings and wherein such dressings are of simpler construction than conventional low or non-adherent dressings.

Accordingly the present invention provides a hypoadherent dressings comprising a fibrous body-facing substrate having a polymeric coating on its body contacting surface.

Fibrous substrates can include both non woven and woven fabrics.

The body contacting surface or surfaces of the substrate can be rendered hypoadherent by the application of a polymeric coating. This considerably reduce the peeling energy compared to uncoated surfaces preferably to where the integrity of the dressing can be maintained on removal. More preferably the peeling energy is not greater than about 100jm$^{-2}$ aptly not more than about 30jm$^{-2}$. The coating may be applied eg. by spraying, onto the body contacting surfaces of the substrate, eg. the outer most strands or fibres of fibrous material. The coated substrate may be pervious to liquids such as water or exudate.

As used herein the peeling energy defines the adhesion between the film and a gelatin substrate. The peeling energy is determined by the method described in J Clinical Materials, Vol 1 (1986) pp9–21 and is expressed in joules per square meter (jm$^{-2}$).

Apt polymers for use in the coatings for the dressings of the invention are those of the urethane class.

Thus in accordance with one embodiment of the invention there is provided a wound dressing comprising a fibrous absorbent layer having a wound contacting face in which the fibres forming the wound contacting face are coated with a polyurethane.

In addition to the urethane residues such polymers will suitably also contain siloxane residues.

Therefore in accordance with another embodiment of the invention there is provided a wound dressing comprising a fibrous absorbent layer having a wound contacting face in which the fibres forming the wound contacting face are coated with a polymer comprising urethane and siloxane residues.

The siloxane residues may be present in the polymer forming the coating or may be part of an polymeric additive which is incorporated, for example by blending, into the main coating polymer.

The polymers for use in the coatings for the dressings of the invention can also contain hydrophobic and or hydrophilic moieties. Preferably the polymers are substantially linear in nature, to confer a desired degree of flexibility in use. However, the coatings for use in the dressings of the invention may comprise polymer blends in order to achieve the desired physical properties. Blends containing up to about 10%, preferably about 5% by weight of a siloxane containing urethane polymer additive can suitably be employed. Preferably such blends comprise a siloxane containing urethane polymer and another polyurethane.

Preferred urethanes are polyether polyurethanes and suitably will be random copolymers.

The ether units may be notionally derivable from alkylene diols eg. ethylene diol and a propylene or butylene diol. Preferably the polyurethane will contain $CH_2CH_2O$—units together with —$CH_2CH_2CH_2O$—, —$CH_2CH(CH_3)O$— or —$CH_2CH_2CH_2CH_2O$—units. More preferably the ether units in the polyurethane will contain —$CH_2CH_2O$—and —$CH_2CH(CH_3)O$—or —$(CH_2)_4O$—or mixtures thereof of which poly —$CH_2CH(CH_3)O$—blocks are preferred. In the preferred polyurethanes the mole ratio of poly(ethylene glycol) to poly[(prop or but)ylene glycol] derivable blocks present in the hydrophilic polyurethanes may vary from 1:1 to 1:30, more suitably from 1:2 to 1:10 and preferably from 1:2.5 to 1:4. The molecular weight of these blocks is aptly from 600 to 60000 and favourably from 900 to 4000, for example 1000 to 2000.

The polyurethane may contain di-isocyanate residues which may be residues of aromatic or aliphatic di-isocyanates such as 4,4'-diphenylmethane di-isocyanate, toluene di-isocyanate, 1,6-hexamethylene di-isocyanate, 4,4'dicyclohexylmethane di-isocyanate or the like. Favoured di-isocyanates for use in the hydrophilic polyurethane of this invention are 4,4'dicyclohexylmethane di-isocyanate (which is preferred) and 4,4'-diphenylmethyl di-isocyanate.

The urethane polymers for use in the coatings of the invention may also contain chain extenders such as diols, diamines or amino alcohols. Typical chain extenders are aliphatic compounds such as ethane diol, butane 1,4-diol or butane 1,4-diamine. Cyclic amines such as piperazine may also be used.

Suitable polyurethanes for use as coatings for the invention may be polyether or polyester polyurethanes and can include thermoplastic polyurethanes such as those described in U.S. patent specification No.

2871218. Examples of such polyurethanes are commercially available under the trade mark 'Estane'.

Aptly, the polyurethane will be a hydrophilic polyurethane which when hydrated contains from 5 to 50% of water, more aptly from 10% to 40% of water and favourably from 20% to 30% of water. Examples of such hydrophilic polyurethanes are disclosed in UK Patent Specification No. 2093190A.

The siloxane residues may be incorporated into either the main coating polyurethanes coatings or into the additives for the main polyurethane. Alternatively, other polymers can be polymerised together with the other precursors for the polymer or additives therefore.

It is preferred to incorporate the siloxane as an additive polymer which is compatible with the main coating polyurethane. Such additive polymers may be polysiloxane-polyurethane copolymers.

The siloxane residues may suitably be derived from siloxane containing materials including polyalkyl siloxanes or copolymers thereof. Preferred siloxane polymers are those based on polydimethyl siloxane.

When incorporated into polyurethane coating or additive systems, the siloxane residues may be co-present with alkylene oxide residues. Thus at least a part of the alkylene oxide component of the final polyurethane may be derived from oligomers containing both the siloxane and alkylene oxide units. Especially suitable oligomers are block copolymers of polyalkylene siloxane, such as polydimethyl siloxane and a polyalkylene polyol such as polyethylene or polypropylene glycol, a mixed polyalkylene polyol or a mixture of such polyalkylene polyols. Especially suitable block copolymer of this class are those marketed under the name Petrarch.

The polymers may be produced under conventional reaction conditions for producing polyurethanes and the final polymer taken up in appropriate solvent for it to be applied as a coating.

The coatings may be applied as a spray onto the wound or body-facing surface. Alternatively the coating may be applied as a discontinuous coating such as a net or pattern coating.

Suitable fibrous substrates include non-woven spun-bonded or spun-laced textiles such as Sontara or open weave textiles such as those marketed under the trade names Keyback, Corovin and Fintex gauzes, non-woven fabrics, and knitted fabrics such as Tricotex.

Dressings may be produced by coating either a single layer or a multiply arrangement of layers of absorbent fibrous material. The hypoadherent coating can be coated on one or more sides of the absorbent layer to provide at least one wound or body contacting surface.

In another embodiment the coated layer or assembly may be employed as a dressing which is intermediate to the wound and another absorbent material such as a foam or another fibrous material eg. layer of a non woven fabric or cotton wool. In one form of this embodiment a composite wound dressing may be formed in situ by first placing a hypoadherent dressing in accordance with the invention, with the coated side contacting the wound, placing an absorbent layer over the top of the applied dressing and securing the composite dressing to the body. In this way the absorbent part of the dressing may be removed and replaced as desired and the hypoadherent layer only removed once the wound has healed. In an alternative form of this embodiment, the absorbent layer may be bonded to or encapsulated by the hypoadherent later. Other layers, eg. liquid impervious barrier sheets may be bonded to the absorbent layer on the surface opposed to the surface bearing the hypoadherent layer.

The amount of coating on the body-contacting surface of the substrate will depend largely on the duty required for the dressing as well as the 'open-ness' of the substrate structure. Where the substrate is required to act as an absorbent or is an intermediate layer between the body and a further layer of absorbent material, the coating weight will be chosen so as not to adversely effect the liquid permeability of the substrate. For hypoadherent, liquid pervious dressings, the coating weight may be upto about 20g/m$^2$ of coating polymer or polymer blend eg. for open-weave structures such as gauze, or upto about 10g/m$^2$ for example where denser textiles are employed. Generally the coating weight may range from 1 to 6 g/m$^2$, typically about 2 or 3g/m$^2$. Higher coating weights may be employed for materials with large void areas or if permeability, particularly initial permeability, is not of paramount importance.

Hypoadherent coatings may be applied onto a portion of an adhesive coated substrate such as a sheet or tape made of fibrous material to provide an adhesive dressing comprising a non-adherent area surrounded by an adhesive coating. The adhesive may suitably be a pressure sensitive adhesive. Preferred forms include a highly moisture permeable non-woven backing layer coated with a discontinuous layer of adhesive and having a centrally disposed strip of hypoadherent polymeric coating. The discontinuity in the adhesive layer will typically be large enough to allow moisture through to the fibrous layer and such discontinuity may be in the form of pores in the adhesives or void areas such as those formed by pattern spreading the adhesive.

Alternatively, sheets of fibrous substrates may be first coated to render them hypoadherent and then adhesive strips applied to one or more pairs of opposed edges.

The dressings of the invention may be packaged, sealed and sterilised by conventional means.

In the treatment of wounds, the dressings of the invention may be applied by contacting the coated side of the dressing of the invention to the wound surface. The dressing may be retained in situ until such time as the dressing is required to be removed.

The invention will now be illustrated by the following examples.

EXAMPLE 1

An additive block terpolymer was prepared by bulk polymerisation of the following components.

| | |
|---|---|
| Petrarch Siloxane Diol - MW1970 (a polydimethyl siloxane/polyethylene glycol block copolymer diol) | 0.015 mole |
| Butane 1,4-Diol | 0.035 mole |
| Desmodur W (Hexamethylene diisocyanate) | 0.050 mole |
| T$_{12}$ (Di-n-butyl tin dilaurate) catalyst | 0.2% by weight |

The Petrarch Siloxane Diol was heated to 60° C. in a 2 liter reaction vessel followed by addition of T$_{12}$ (Di-n-butyl tin dilaurate) catalyst and the Desmodur W (Hexamethylene diisocyanate).

The reaction mixture was heated at 60° C. for 1 hour with constant stirring of the reactants.

At the end of this time the butane 1,4-diol was added and the reactants stirred and heated at 60° C. for a further 2 hours. after cooling (over night) the reaction product was taken up into a mixture of methylene dichloride and industrial methylated spirit (5:4 v/v) as 2% by weight solution.

The solution was sprayed, using an air-gun onto a commercially available Keyback open weave sheet at a coating weight of about 6gsm.

Gelatin was cast onto the coated sheet and an uncoated sample of Keyback and left to dry for 24 hours at 35° C. On testing for peel energy the coated sample readily peeled from the gelatin, whereas with the uncoated sample, the textile could not be removed but disintegrated when peeling force was applied.

EXAMPLE 2 a) Additive Preparation

A block terpolymer was prepared as described in Example 1 and taken up as a 28.8% by weight solution in a methylene dichloride/industrial methylated spirits mixed solvent.

b) Main Polymer

A piperazine chain extended polyurethane was prepared from the following precursors:
Polethylene Glycol (M.wt 1585) 1585 gm
Polypropylene Glycol (m.wt 1021) 6125.5gm
Piperazine 603 gm
Hexamethylene Diisocyanate 3794.4gm
Di-n-butyl tin dilaurate Catalyst 24.2gm The polyurethane glycol was melted at 90° C. and weighed into a resin reactor flask together with the polypropylene glycol and the isocyanate. The flask was then closed, the contents heated in a water bath to 90° C. and stirred until the reaction mass was homogenous. The catalyst was added and the reactants stirred for a further 30 minutes whereupon the flask was allowed to cool to 60° C.

765gm of dichloromethane and 235gm of t-butanol were mixed to form a solvent and 900gm of the solvent mixture added to the resin flask. The contents of the flask were heated to 60° C. The piperazine was dissolved up in the remaining 100gm of solvent and the solution added dropwise into the resin flask.

The reaction mixture was then heated under relux, with stirring, at 60° C. for a further 2 hours.

On completion of the reaction the polymer solution was bottled and sealed. The solids content of the polymer solution was 15.6% by weight.

c) Polymer Blend

A polymer blend was prepared by mixing the following:
Polymer Solution 115.4gm
Additive Polymer Solution 6.9gm
Dichloromethane 877.7gm
Methanol 50.0gm The ratio of main polymer to additive polymer was 9:1 and the solids content of the blend was 1.9% by weight.

Preparation of Dressing

The polymer blend was diluted with a further amount of Dichloromethane to give a 1% solution of the polymer blend. The polymer solution was then applied by air brush to one surface of each of the following materials:

| | |
|---|---|
| Corovin | A spun-bonded heat embossed polypropylene non-woven (Corovin GmbH) |
| Sontara 8010 | A spun-laced polyester staple fibre (40 g/m$^2$) non-woven (Du Pont) |
| Gauze | |
| Tricotex | A viscose-rayon knitted fabric (Smith & Nephew) |

The coating weight of polymer on the substrate was about 2 gsm.

Gelatin test

A 40% by weight solution of gelatin in distilled water was produced by dissolving 40 gms of gelatin in 60 gms of water at 70° C. The hot gelatin solution was cast into 60×16 mm blocks.

Samples of the coated fibrous materials and uncoated materials were applied, each to a gelatin block. The uncoated Corovin, Sontara and Tricotex fabrics each had obvious differences in the appearance of their two surfaces and the smoother face was choosen as the test face against the gelatin. The coated surface of the dressings of the invention was applied to the gelatin surface.

The blocks were placed in an oven a 37° C. for 24 hours to set and dry the gelatin. After removal from the oven the fabric material was peeled back manually a short distance to expose a section of gelatin which was gripped in the jaws of a Instron 1195 testing machine. The tab of the fabric was taken up through 180° and held in the upper jaws. Peeling was performed at a cross-head speed of 100 mm per minute. The peeling force (in Newtons) was recorded.

The peeling energy $\theta$ (Jm$^{-2}$) for each material was calculated according to the equation:

$$\theta = 2P/b$$

Where P is the peeling force (Newtons) and b the width of the peeling member.

The peel energy for the coated and uncoated control samples is shown in the following table:

| Material | Peeling Energy (Coated) Jm$^{-2}$ | Peeling Energy (Uncoated) Jm$^{-2}$ |
|---|---|---|
| Corovin | 125 | No peeling, failed cohesively. |
| Sontara 8010 | 384 | No peeling, failed cohesively |
| Gauze | 79 | Slight peeling, then cohesive failure |
| Tricotex | 450 | 1046 |

From these results it is apparent that the dressings of the present invention require considerably less peeling energy than the counterpart uncoated control samples.

I claim:

1. A hypoadherent dressing comprising a fibrous body-facing substrate having a liquid pervious polymer coating on its body-contacting surface, wherein said polymer coating comprises a polyurethane containing siloxane residues.

2. A dressing according to claim 1 wherein said polymer coating is a blend of polymers comprising said polyurethane containing siloxane residues.

3. A dressing according to claim 2 wherein the blend comprises a major amount of a first polyurethane and a minor amount of a urethane-siloxane copolymer.

4. A dressing according to claim 3, wherein the amount of said urethane-siloxane copolymer in said blend does not exceed 10% by weight.

5. A dressing according to claim 3 wherein the first polyurethane is an amine chain extended polyurethane.

6. A dressing according to claim 1 wherein the polyurethane is an amine chain extended polyurethane.

7. A dressing according to claim 1, in which the weight of said polymer coating does not exceed 10 $gm^{-2}$.

8. A dressing according to claim 1 wherein the weight of polymer coating is from 1 to 6 $g\ m^{-2}$.

9. A dressing according to claim 1 wherein a layer of absorbent material is bonded to the non-body contacting surface of the substrate.

10. A dressing according to claim 1 wherein the body-facing substrate encapsulates a layer of absorbent material.

11. A dressing pack comprising a sterilised dressing of claim 1, sealed within a package.

12. A method of treating wounds comprising applying the body-contacting surface of a dressing according to claim 1 to the surface of the wound.

* * * * *